United States Patent
Alagappan et al.

(10) Patent No.: US 8,415,950 B2
(45) Date of Patent: Apr. 9, 2013

(54) SYSTEM AND METHOD FOR PARALLEL TRANSMISSION IN MR IMAGING

(75) Inventors: Vijayanand Alagappan, Streetsboro, OH (US); Fraser John Laing Robb, Aurora, OH (US); Victor Taracila, Beachwood, OH (US)

(73) Assignee: General Electric Company, Schenectady, NY (US)

( * ) Notice: Subject to any disclaimer, the term of this patent is extended or adjusted under 35 U.S.C. 154(b) by 533 days.

(21) Appl. No.: 12/820,246

(22) Filed: Jun. 22, 2010

(65) Prior Publication Data
US 2011/0309832 A1     Dec. 22, 2011

(51) Int. Cl.
*G01V 3/00* (2006.01)
(52) U.S. Cl.
USPC ........................................................ 324/307
(58) Field of Classification Search .......... 324/300–322; 600/407–445
See application file for complete search history.

(56) References Cited

U.S. PATENT DOCUMENTS

| | | | |
|---|---|---|---|
| 6,154,029 A * | 11/2000 | Miyamoto et al. | 324/312 |
| 7,053,615 B2 | 5/2006 | Lazar et al. | |
| 7,323,873 B2 * | 1/2008 | Yamazaki | 324/309 |
| 7,394,253 B2 * | 7/2008 | Okamoto et al. | 324/318 |
| 8,232,802 B2 * | 7/2012 | Okamoto et al. | 324/318 |
| 2010/0039113 A1 | 2/2010 | Vartiovaara | |
| 2012/0223709 A1 * | 9/2012 | Schillak et al. | 324/309 |

OTHER PUBLICATIONS

Wang et al., "B1 Homogenization in MRI by Multi-layer Coupled Coils," IEEE TMI, 2008, pp. 1-4.

* cited by examiner

*Primary Examiner* — Brij Shrivastav
(74) *Attorney, Agent, or Firm* — Ziolkowski Patent Solutions Group, SC

(57) ABSTRACT

A system and method for selectively operating an array of RF receive coils in a transmit mode is disclosed. The system includes an RF transmit coil configured to generate an RF field that excites nuclei of a subject to generate RF resonance signals, an array of RF receive coils to receive the RF resonance signals, and a detuning circuit coupled to each RF receive coil in the array of RF receive coils that is selectively switched between a disabled and an enabled state to control a resonance and impedance of the RF receive coil. Each RF receive coil is caused to receive RF resonance signals when its respective detuning circuit is in the disabled state and is caused to modify an amplitude and phase of the RF field generated by the RF transmit coil when its respective detuning circuit is in the enabled state.

21 Claims, 3 Drawing Sheets

SYSTEM AND METHOD FOR PARALLEL TRANSMISSION IN MR IMAGING

BACKGROUND OF THE INVENTION

Embodiments of the invention relate generally to a system and method for MR imaging and, more particularly, to a system and method for selectively and dynamically operating an array of RF receive coils in a transmit mode to generate a local RF field that adds up with the RF field generated by a whole body transmit coil, such that the transverse MR magnetization has the desired amplitude and phase.

When a substance such as human tissue is subjected to a uniform magnetic field (polarizing field $B_0$), the individual magnetic moments of the spins in the tissue attempt to align with this polarizing field, but process about it in random order at their characteristic Larmor frequency. If the substance, or tissue, is subjected to a transverse RF magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals is digitized and processed to reconstruct the image using one of many well known reconstruction techniques.

In order to generate high quality images that minimize contrast and sensitivity variations, MRI applications require a uniform $B_1$ field. Traditional quadrature-driven volume coils used for $B_1$ field excitation provide limited uniformity of the field, especially as the strength/intensity of the magnetic field is increased (e.g., 3 T or 7 T magnetic fields). Therefore, the ability to generate a uniform $B_1$ field is important for full realization of the potential of MRI applications utilizing a higher field strength.

Recently, several methods have been proposed in RF coil design to homogenize the $B_1$ field. One such method for homogenizing the $B_1$ field is parallel transmission. In existing MRI systems, parallel transmission corrects for the transmit $B_1$ field inhomogeneity by having control over the amplitude and phase of individual transmit elements in a multi-channel transmit array coil, otherwise known as passive RF shimming. Parallel transmission further corrects for the transmit $B_1$ field inhomogeneity by tailoring the magnetization by using spatially tailored RF pulses along with the gradients, otherwise known as active parallel transmit.

There are, however, several drawbacks to implementing existing methods of parallel transmission for purposes of homogenizing the $B_1$ field. For example, as stated above, implementation of parallel transmission requires a multi-element transmit array coil, with the individual transmit elements needing to be well decoupled. For the multi-element transmit array, individual exciter boxes for fine control of the RF pulse waveform are needed, along with independent RF amplifiers for each element in the transmit array coil. Providing such a multi-element transmit array coil, and its associated elements, significantly increases the hardware cost for an MRI system.

It would therefore be desirable to have a system and method that provides a uniform $B_1$ field without the need for a multi-element transmit array coil and associated components typically required for parallel transmission.

BRIEF DESCRIPTION OF THE INVENTION

The invention provides a system and method for selectively and dynamically operating an array of RF receive coils in a transmit mode to generate a local RF field that adds up with the RF field generated by a whole body transmit coil, such that the transverse MR magnetization has the desired amplitude and phase. A detuning circuit is coupled to each RF receive coil in the array of RF receive coils that is selectively switched between a disabled and an enabled state to control a resonance and impedance of the RF receive coil, thereby selectively causing the array of RF receive coils to operate in either a transmit or a receive mode.

In accordance with one aspect of the invention, an MRI system includes a main magnet having a bore therethrough, a plurality of gradient coils positioned about the bore of the main magnet, and an RF transmit coil disposed within the bore of the main magnet and configured to generate an RF field, with the RF field exciting nuclei of a subject positioned within the bore to generate RF resonance signals. The MRI system also includes an array of RF receive coils disposed within the bore of the main magnet and positioned relative to the RF transmit coil so as to receive the RF resonance signals and a detuning circuit coupled to each RF receive coil in the array of RF receive coils that is selectively switched between a disabled and an enabled state to control a resonance and impedance of the RF receive coil. Each RF receive coil is caused to receive RF resonance signals when its respective detuning circuit is in the disabled state and is caused to modify an amplitude and phase of the RF field generated by the RF transmit coil when its respective detuning circuit is in the enabled state.

In accordance with another aspect of the invention, a method for parallel transmission in an MRI system includes causing a whole-body RF transmit coil to generate a first RF field during a transmit cycle of operation of the MRI system and causing an array of RF receive coils to generate a second time-varying RF field during the transmit cycle of operation of the MRI system. Causing the array of RF receive coils to generate the second time-varying RF field further includes enabling a detuning circuit coupled to the array of RF receive coils and selectively and dynamically controlling the detuning circuit to control an impedance and an off resonance in the detuning circuit, thereby also controlling an impedance and an off resonance in the array of RF receive coils so as to cause the array of RF receive coils to generate the second time varying RF field during the transmit cycle of operation of the MRI system. Upon completion of the transmit cycle, the method also includes disabling the detuning circuit so as to cause the array of RF receive coils to receive RF resonance signals emitted from a subject generated in response to the first RF field and the second time-varying RF field and storing the received RF resonance signals on a computer readable storage medium.

In accordance with yet another aspect of the invention, an MRI system includes a main magnet having a bore therethrough, a plurality of gradient coils positioned about the bore of the main magnet, and an RF transmit coil disposed within the bore of the main magnet and configured to generate a $B_1$ field during a transmit cycle of the MRI system, with the $B_1$ field exciting nuclei of a subject positioned within the bore to generate RF resonance signals. The MRI system also includes an array of RF receive coils disposed within the bore of the main magnet and within a volume surrounded by the RF transmit coil and a detuning circuit arrangement coupled to the array of RF receive coils to selectively cause the array of RF receive coils to operate in one of a transmit mode and a receive mode. The detuning circuit arrangement is configured to operate in an enabled state during the transmit cycle of the MRI system so as to dynamically control impedance and off resonance in the array of RF receive coils, with operation of the detuning circuit arrangement in the enabled state causing the array of RF receive coils to generate a local $B_1$ field having a desired amplitude and phase. The detuning circuit arrangement is further configured to operate in a disabled state during a receive cycle of the MRI system, with operation of the detuning circuit arrangement in the disabled state causing the array of RF receive coils to receive the RF resonance signals generated in response to the $B_1$ field and the local $B_1$ field.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

Figure 1:
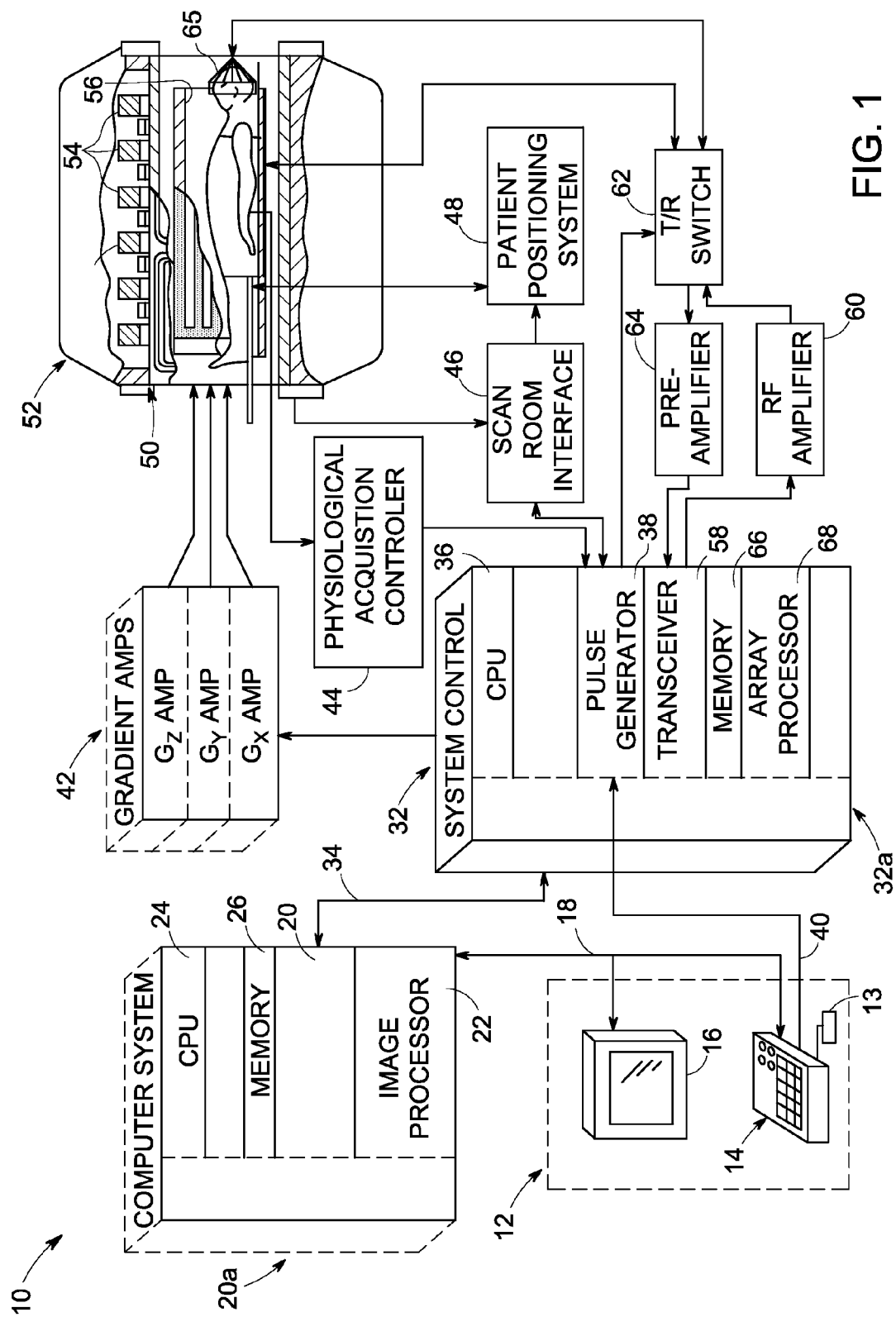
FIG. 1 is a schematic block diagram of an MR imaging system incorporating the invention.

Referring to FIG. 1, the major components of a preferred magnetic resonance imaging (MRI) system 10 incorporating an embodiment of the invention are shown. The operation of the system is controlled from an operator console 12, which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired location for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52, which includes a polarizing magnet 54 and a single, whole-body RF coil 56 that, according to an exemplary embodiment of the invention, functions as a transmit coil to generate a transverse RF magnetic field (excitation field $B_1$) which is in the x-y plane. A transceiver module 58 in the system control 32 produces pulses which are amplified by an RF amplifier 60 and coupled to the transmit coil 56 by a transmit/receive switch 62. The resulting signals emitted by the excited nuclei in the patient may be sensed by a separate array of RF receiver coils 65, such a birdcage-type surface array coil, for example, and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the transmit coil 56 during the transmit mode and to connect the preamplifier 64 to the receive coil 65 during the receive mode.

The MR signals picked up by the array of receive coils 65 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory. In response to commands received from the operator console 12, this image data may be archived in long term storage or it may be further processed by the image processor 22 and conveyed to the operator console 12 and presented on the display 16.

Figure 2:
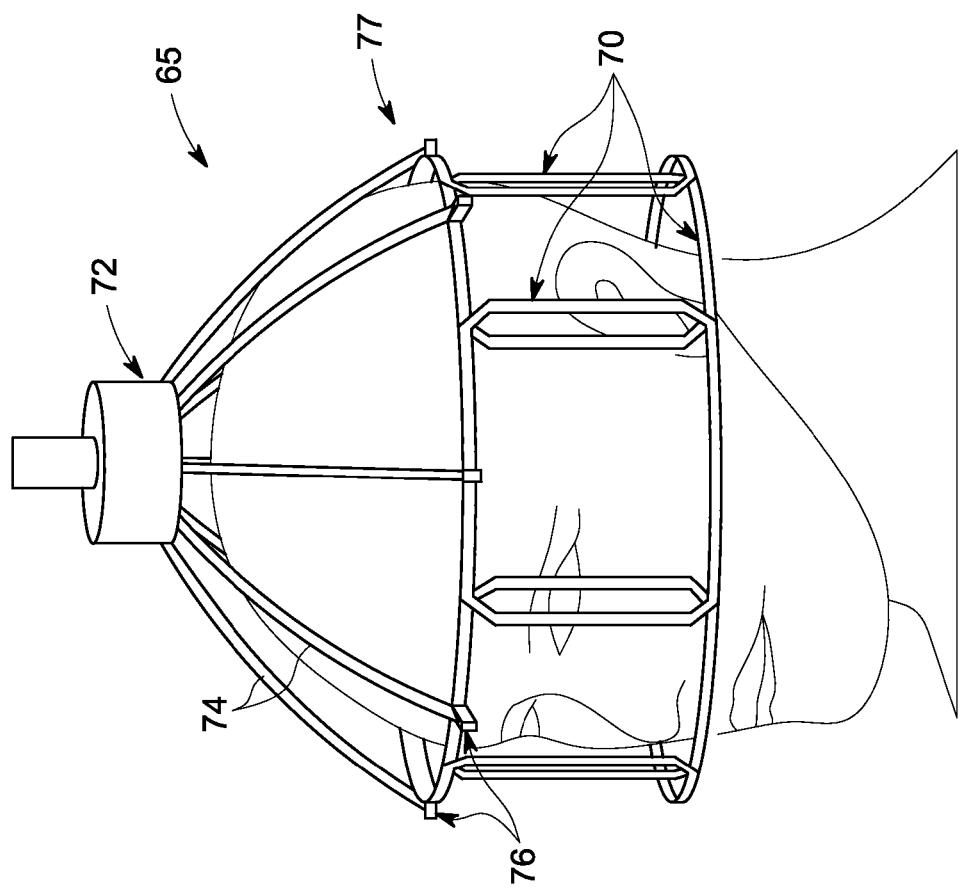
FIG. 2 is a prospective view of an array of RF receive coils positioned relative to a patient, with the array of RF receive coils having detuning circuits coupled thereto according to an embodiment of the invention.

Referring now to FIG. 2, a perspective view of the array of receive coils 65 relative to a patient is shown, according to an embodiment of the invention. The array of receive coils 65 includes a plurality of individual coil elements or loops 70 therein having a desired radius. Operably connected to the array of receive coils 65 is control electronics 72 that function to control a supply of power to the array 65. Control electronics 72 are coupled to loops 70 of the array 65 by way of connectors 74.

Also included in the array 65, corresponding to each of coil loops 70, is DC circuitry in the form of what will be termed an "active detuning circuit," generally identified at 76. The detuning circuit 76 is a parallel resonance circuit that is connected in series with a respective coil loop 70 in array 65, and is controllable so as to selectively modify impedance to current flowing in the respective coil loop 70, as will be explained in greater detail below. That is, detuning circuit 76 can be selectively enabled and disabled during transmit and receive cycles, respectively, to decrease and increase the impedance to current flowing in the respective coil loop 70. An arrangement 77 of detuning circuits 76 is provided, such that a detuning circuit 76 is coupled to each of the coil loops 70.

It is noted that a typical "detuning circuit" for a receive coil will normally function to completely decouple the receive coil from the surrounding electromagnetic field during a transmit cycle/pulse. However, according to an embodiment of the present invention, detuning circuit 76 functions to selectively "tune" and "offtune" a coil loop 70 from the surrounding electromagnetic field. That is, when detuning circuit(s) 76 are disabled during a receive cycle, the array of receive coils 65 functions as a typical receive array (i.e., made low-impedance) to sense signals emitted by the excited nuclei in the patient. However, when detuning circuit(s) 76 are enabled during a transmit cycle, the array of receive coils 65 are offtuned from the whole-body transmit coil (i.e., the array of receive coils 65 is tuned away or "off" from the Larmor frequency) to function as a local transmit coil that is added to the $B_1$ field generated by the whole body transmit coil 56 (FIG. 1), so as to control the amplitude and phase of the induced field formed by the transmit coil. Specifically, the offtuning of detuning circuit(s) 76, via enabling thereof, causes the detuning circuit(s) to have an inductive impedance rather than a large real impedance, such that currents are induced into the array of the receive coils 65 from the whole body transmit coil 56. The array of the receive coils 65 is thus caused to function as a local transmit coil that generates a local $B_1$ field that modifies the amplitude and phase of the induced $B_1$ field generated by transmit coil 56. Accordingly, the array of the receive coils 65 can be termed as a Field Enhancing Receive Array (FERArray) that provides for parallel transmission.

Figure 3:
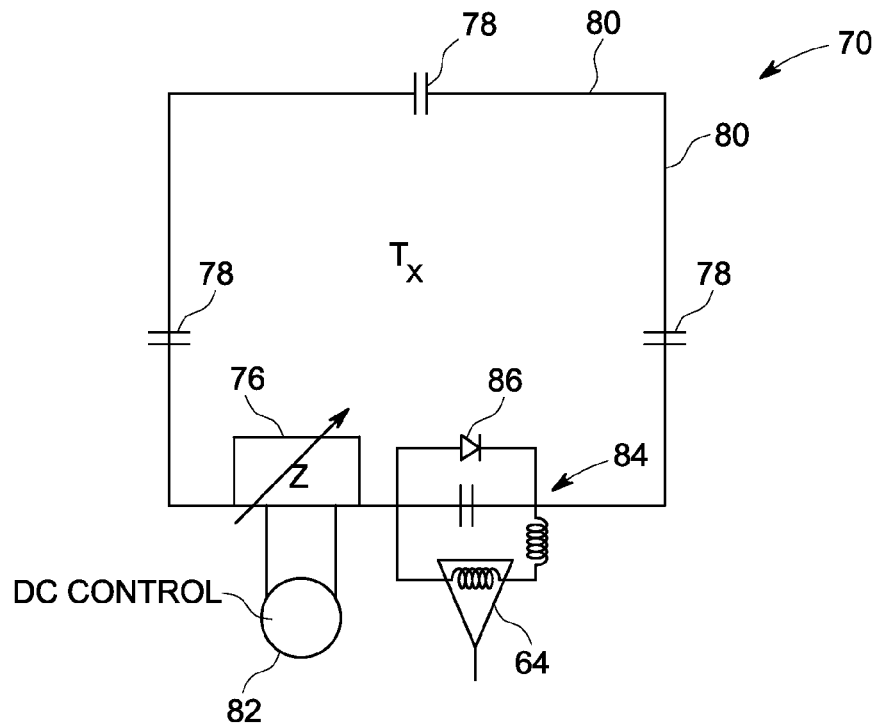
FIG. 3 is a schematic diagram of an RF receive coil having a detuning circuit coupled thereto according to an embodiment of the invention.

Implementation of detuning circuit 76 relative to a receive coil loop 70 is illustrated in the schematic diagram of FIG. 3. As shown therein, coil loop 70 includes tuning capacitors 78 connected between coil traces 80. Detuning circuit 76 is positioned along coil traces 80 and is connected to a DC control(s) 82 that functions to enable/disable the detuning circuit 76 and control operation thereof to vary off resonance and impedance in coil loop 70. Also positioned along coil traces 80 of coil loop 70 is a preamp decoupling circuit 84 that includes a diode 86 therein. Preamp decoupling circuit 84 functions to selectively connect and disconnect a preamplifier 64 (also shown in FIG. 1), by way of diode 86, to coil loop 70 during receive and transmit cycles, respectively.

Figure 4:
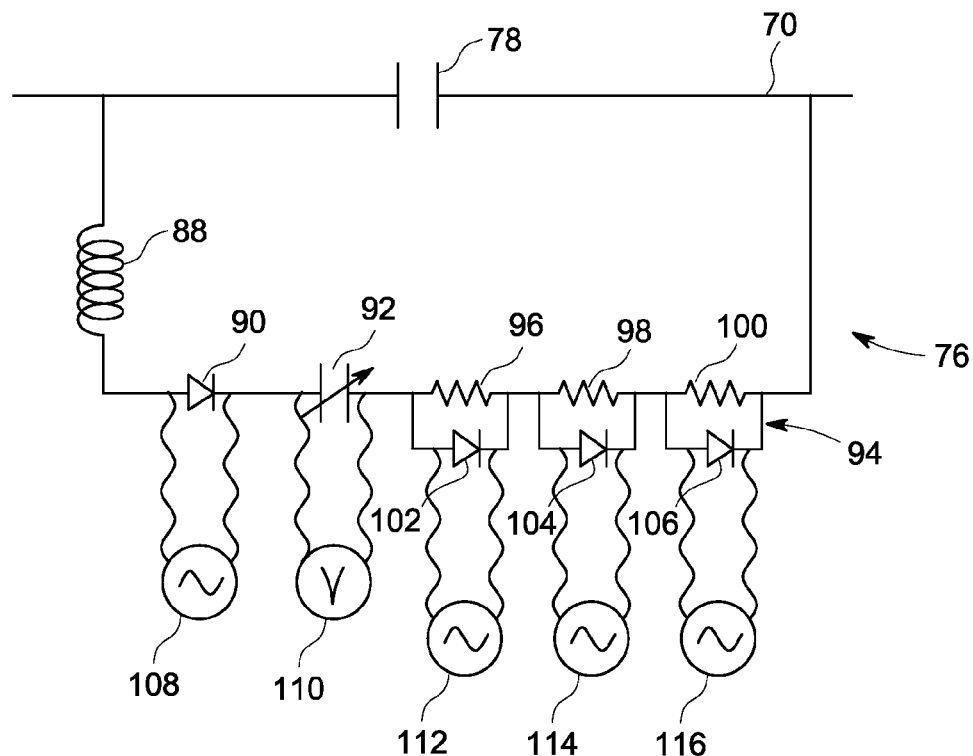
FIG. 4 is a circuit schematic diagram of the detuning circuit according to an embodiment of the invention.

Referring now to FIG. 4, a circuit schematic of detuning circuit 76 is shown according to an exemplary embodiment of the invention. Detuning circuit 76 includes an inductor 88, a diode 90 (i.e., "enabling diode"), a varactor or varicap diode 92, and a variable or stepped attenuator 94 that further includes a plurality of high power resistors 96, 98, 100 and diodes 102, 104, 106. Also included in detuning circuit 76 are a plurality of DC controls 108-116 that function to control operation of diode 90, varactor diode 92, and variable attenuator 94. While a specific arrangement of inductor 88, diode 90, varactor diode 92, and variable attenuator 94 is shown as forming detuning circuit 76, it is recognized that detuning circuit 76 may be varied in its exact arrangement and components included therein, and may vary from the embodiment shown in FIG. 4.

In operation of detuning circuit 76, DC control 108 functions to control diode 90 for purposes of enabling and disabling detuning circuit 76. When detuning circuit 76 is in a disabled state during a receive cycle, diode 90 is controlled by DC control 108 such that detuning circuit 76 effectively operates as a capacitor (i.e., capacitor 78). With detuning circuit 76 disabled, the coil loop 70 thus operates as a typical receive coil element, having a desired resonance and impedance (i.e., operates in a receive mode).

However, when detuning circuit 76 is enabled during a transmit cycle, diode 90 is controlled by DC control 108 to provide for varying of the impedance and the off resonance (as a function of capacitance) of the receive coil loop 70, such that receive coil loop 70 can be controlled to generate a local $B_1$ field (i.e., operates in a transmit mode). When detuning circuit 76 is enabled during a transmit cycle/phase of the MRI system (i.e., during transmission by transmit coil 56, FIG. 1), inductor 88 is switched into parallel with tuning capacitor 78, such that the tuning capacitor 78 and inductor 88 are made to form a parallel resonant circuit of high impedance, for "blocking" current flow in the coil loop 70. Additionally, DC control 110 functions to control varactor diode 92 so as to control the off resonance of detuning circuit 76 by changing capacitance therein. Furthermore, DC controls 112, 114, 116 function to control operation of variable attenuator 94, by selectively controlling operation of diodes 102, 104, 106 so as to increase or decrease resistance in the attenuator 94 by way of resistors 96, 98, 100. Controlling of attenuator 94 by way of DC controls 112, 114, 116 thus controls a Q factor of the impedance by adding different combinations of resistors 96, 98, 100. The amplitude and phase of the local $B_1$ field generated by receive coil loop 70 can thus be controlled via selective control of detuning circuit 76, so as to perturb the induced $B_1$ field formed by the transmit coil 56 (FIG. 1) in a desired manner by adding the local $B_1$ field to the $B_1$ field generated by the transmit coil 56.

The ultimate $B_1$ field generated via the interaction of whole body transmit coil 56 and the array of receive coils 65 will depend on the superposition of the incident transmit coil 56 and the secondary field coming from receive coil array 65 in the off-tuned state. According to an example set forth below, it is assumed that the incident magnetic field generated by the transmit coil 56 is $B_i$ (which can be linearly or circularly polarized), with $B_i$ typically being under 50 µT.

For a coil loop 70 of receive coil array 65, the voltage generated along its perimeter will be:

$$E_{emf} = -\frac{\partial}{\partial t}\int_\Sigma B_i \, dS, \qquad [\text{Eqn. 1}]$$

where dS represents the infinitesimal piece of the surface of the loop $\Sigma$.

Knowing that the magnetic field is frequency dependent, $B_i = B_{i0} e^{-j\omega_0 t}$, and with $\omega_0 = 2\pi f_0$ we can write [Eqn. 1] for a circular coil loop 70 of radius $r_0$ as:

$$E_{emf} = j\pi r_0^2 \omega_0 B_{i0} n e^{-j\omega t} \qquad [\text{Eqn. 2}],$$

where n is the normal to the surface of the coil loop 70.

If the coil loop 70 has collective blocking impedance, $Z_l$, then the current generated in the loop will be:

$$I_l = \frac{E_{emf}}{Z_l} = j\frac{\pi r_0^2 \omega_0 B_{i0} n}{Z_l} e^{-j\omega t}. \qquad [\text{Eqn. 3}]$$

On the central axis of the coil loop 70 (e.g., the x-axis) the magnetic field can be simply written as:

$$B_{x,center} = \frac{\mu_0}{2} \frac{r_0^2}{(r_0^2 + x^2)^{3/2}} I_l. \qquad [\text{Eqn. 4}]$$

Then the total value of the total magnetic field from [Eqn. 3] with [Eqn. 4] will be:

$$B_{tot} = B_{i0} + j\frac{\mu_0}{2}\frac{\pi r_0^2 \omega_0 B_{i0} n}{Z_l}\frac{r_0^2}{(r_0^2 + x^2)^{3/2}}. \quad [\text{Eqn. 5}]$$

Factoring out the incident field generated by transmit coil 56, we can, on the normal to the coil, have:

$$B_{tot} = B_{i0}n\left(1 + j\frac{\mu_0}{2}\frac{\pi r_0^2 \omega_0}{Z_l}\frac{r_0^2}{(r_0^2 + x^2)^{3/2}}\right). \quad [\text{Eqn. 6}]$$

We can then define a field enhancement function (FEF) as a function of depth according to:

$$f(x) = \frac{\mu_0}{2}\frac{\pi r_0^4 \omega_0}{(r_0^2 + x^2)^{3/2}}, \quad [\text{Eqn. 7}]$$

with the Field Enhancement Function representing the product between sensitivity of the receive coil loop 70 multiplied by its surface area and system frequency and being measured in units of resistance.

Therefore, [Eqn. 6] will become:

$$B_{tot} = B_{i0}n\left(1 + j\frac{f(x)}{Z_l}\right). \quad [\text{Eqn. 8}]$$

The impedance of the coil loop 70 is comprised of the real resistive losses and an imaginary part. If we will separate the fixed impedance of the receiver coil loop 70 (i.e., the intrinsic resistance of the load and traces) from the impedance of the detuning circuit 76, with $Z_l$ being defined by real and imaginary parts ($R_l$ and $jX_l$) of the fixed impedance of the receiver coil loop 70 and by real and imaginary parts ($R_{bl}(t)$ and $X_{bl}(t)$) of the controllable impedance of detuning circuit 76, then:

$$B_{tot}(x, t) = B_{i0}n\left(1 + j\frac{f(x)}{R_l + R_{bl}(t) + jX_{bl}(t)}\right). \quad [\text{Eqn. 9}]$$

The parameter t, which stands for time variation, is then introduced. The receiver coil and load intrinsic impedance is dependent on the resistance $R_l$, which increases with a size of coil loop 70. Typically, it can vary between 10 and 30 Ohm for respectively small and large elements. Eqn. 9 shows that with appropriate choice of real and imaginary functions for the detuning circuit 76, one can modify the original $B_1$ field generated by transmit coil 56 both in phase and magnitude.

According to embodiments of the invention, it is recognized that the array of receive coils 65 can be controlled by way of detuning circuit(s) 76 to provide for either passive RF shimming type transmission (i.e., passive parallel transmission) or active parallel transmission with gradients. To use the array of receive coils 65 for passive parallel transmission, the off resonance in the detuning circuit(s) 76 would be set at some fixed point during transmit with the whole-body coil, instead of being dynamically changed. For example, the array of receive coils 65 could be used for passive parallel transmission by fixing the capacitance of varactor diode 92 via DC control 110 (FIG. 4). To use the array of receive coils 65 for active parallel transmission, the off resonance in the detuning circuit(s) 76 would be dynamically controlled during transmit with the whole-body coil. For example, the array of receive coils 65 could be used for active parallel transmission by dynamically changing the capacitance of varactor diode 92 via DC control 110 (FIG. 4).

Thus, according to embodiments of the invention, the array of receive coils 65 are not decoupled from the surrounding electromagnetic field during a transmit phase/cycle of the MR sequence, but rather are controlled by way of detuning circuit(s) 76 so as to focus the power from transmit coil 56 in a controlled way such that the magnetization tipping can be improved considerably.

Beneficially, controlling of the impedance in the array of receive coils 65 by way of detuning circuit(s) 76, results in an array with no intercoil coupling issues. That is, each coil loop 70 has a relatively high impedance during a transmit phase, such that the field from one coil loop cannot induce a current on the other coil loop. Furthermore, since these impedances in the array of receive coils 65 are controlled by DC signals (e.g., from DC controls 108-116), high fidelity on the induced field by can be achieved depending on the quality of, for example, the varactor diode 92 and the variable attenuator 94 in detuning circuit(s) 76.

Inclusion of detuning circuit(s) 76 in the array of receive coils 65 provides for parallel transmission in the MRI system 10, as the array 65 operates as a local transmit coil during the transmit phase/cycle of the MR sequence to generate a local $B_1$ field that modifies the original $B_1$ field generated by transmit coil 56 both in phase and magnitude. This modification of the $B_1$ field is done without shaping the RF pulse waveform in MHz range, as instead the induced field is shaped by changing the impedance and the off resonance of the array of receive coils 65 by way of detuning circuit(s) 76. This eliminates the need for individual exciter boxes and independent RF amplifiers typically necessary for parallel transmission with a multi-element transmit array coil, thereby significantly reducing the hardware cost for the MRI system while still providing for parallel transmission.

A technical contribution for the disclosed system and method is that it provides for dynamically controlling the impedance and off resonance of an array of RF receive coils by way of a detuning circuit. The detuning circuit provides for selective operation of the array of RF receive coils in a transmit mode to generate a local RF field that modifies a RF field generated by a whole body transmit coil, such that an RF field having a desired amplitude and phase can be formed.

Therefore, according to one embodiment of the invention, an MRI system includes a main magnet having a bore there through, a plurality of gradient coils positioned about the bore of the main magnet, and an RF transmit coil disposed within the bore of the main magnet and configured to generate an RF field, with the RF field exciting nuclei of a subject positioned within the bore to generate RF resonance signals. The MRI system also includes an array of RF receive coils disposed within the bore of the main magnet and positioned relative to the RF transmit coil so as to receive the RF resonance signals and a detuning circuit coupled to each RF receive coil in the array of RF receive coils that is selectively switched between a disabled and an enabled state to control a resonance and impedance of the RF receive coil. Each RF receive coil is caused to receive RF resonance signals when its respective detuning circuit is in the disabled state and is caused to modify an amplitude and phase of the RF field generated by the RF transmit coil when its respective detuning circuit is in the enabled state.

According to another embodiment of the invention, a method for parallel transmission in an MRI system includes causing a whole-body RF transmit coil to generate a first RF field during a transmit cycle of operation of the MRI system and causing an array of RF receive coils to generate a second time-varying RF field during the transmit cycle of operation of the MRI system. Causing the array of RF receive coils to generate the second time-varying RF field further includes enabling a detuning circuit coupled to the array of RF receive coils and selectively and dynamically controlling the detuning circuit to control an impedance and an off resonance in the detuning circuit, thereby also controlling an impedance and an off resonance in the array of RF receive coils so as to cause the array of RF receive coils to generate the second time varying RF field during the transmit cycle of operation of the MRI system. Upon completion of the transmit cycle, the method also includes disabling the detuning circuit so as to cause the array of RF receive coils to receive RF resonance signals emitted from a subject generated in response to the first RF field and the second time-varying RF field and storing the received RF resonance signals on a computer readable storage medium.

According to yet another embodiment of the invention, an MRI system includes a main magnet having a bore there through, a plurality of gradient coils positioned about the bore of the main magnet, and an RF transmit coil disposed within the bore of the main magnet and configured to generate a $B_1$ field during a transmit cycle of the MRI system, with the $B_1$ field exciting nuclei of a subject positioned within the bore to generate RF resonance signals. The MRI system also includes an array of RF receive coils disposed within the bore of the main magnet and within a volume surrounded by the RF transmit coil and a detuning circuit arrangement coupled to the array of RF receive coils to selectively cause the array of RF receive coils to operate in one of a transmit mode and a receive mode. The detuning circuit arrangement is configured to operate in an enabled state during the transmit cycle of the MRI system so as to dynamically control impedance and off resonance in the array of RF receive coils, with operation of the detuning circuit arrangement in the enabled state causing the array of RF receive coils to generate a local $B_1$ field having a desired amplitude and phase. The detuning circuit arrangement is further configured to operate in a disabled state during a receive cycle of the MRI system, with operation of the detuning circuit arrangement in the disabled state causing the array of RF receive coils to receive the RF resonance signals generated in response to the $B_1$ field and the local $B_1$ field.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An MRI system comprising:
    a main magnet having a bore there through;
    a plurality of gradient coils positioned about the bore of the main magnet;
    an RF transmit coil disposed within the bore of the main magnet and configured to generate an RF field, the RF field exciting nuclei of a subject positioned within the bore to generate RF resonance signals;
    an array of RF receive coils disposed within the bore of the main magnet and positioned relative to the RF transmit coil so as to receive the RF resonance signals; and
    a detuning circuit coupled to each RF receive coil in the array of RF receive coils and being selectively switched between a disabled and an enabled state to control a resonance and impedance of the RF receive coil;
    wherein each RF receive coil is caused to receive RF resonance signals when its respective detuning circuit is in the disabled state; and
    wherein each RF receive coil is caused to modify an amplitude and phase of the RF field generated by the RF transmit coil when its respective detuning circuit is in the enabled state.

2. The MRI system of claim 1 wherein the detuning circuit is in the disabled state during a receive phase of operation of the MRI system and is in the enabled state during a transmit phase of operation of the MRI system.

3. The MRI system of claim 1 wherein each detuning circuit is configured to offtune a respective RF receive coil to have an inductive impedance when in the enabled state, such that current is induced in the respective RF receive coil by the RF transmit coil so as to cause the respective RF receive coil to generate a local RF field.

4. The MRI system of claim 3 wherein the local RF field generated by each RF receive coil in the array of RF receive coils is added to the RF field generated by the RF transmit coil.

5. The MRI system of claim 1 wherein each detuning circuit is configured to selectively provide for passive parallel transmission and active parallel transmission state for its respective RF receive coil, wherein the detuning circuit sets a fixed off resonance value for its respective RF receive coil for passive parallel transmission and dynamically adjusts an off resonance value for its respective RF receive coil for active parallel transmission.

6. The MRI system of claim 1 wherein the detuning circuit comprises:
    a diode configured to enable and disable the detuning circuit;
    a varactor diode to modify a capacitance in the detuning circuit, thereby controlling resonance of the detuning circuit;
    a variable attenuator to control impedance in the detuning circuit; and
    a DC control system configured to generate DC signals to control each of the diode, the varactor diode, and the variable attenuator.

7. The MRI system of claim 6 where the variable attenuator comprises:
    a plurality of resistors; and
    a plurality of diodes, wherein each of the plurality of diodes is positioned in parallel with a respective resistor in the plurality of resistors;
    wherein the DC control system selectively controls each of the plurality of diodes so as to control the impedance of the variable attenuator.

8. The MRI system of claim 1 wherein the detuning circuit is configured to dynamically control the impedance of the RF receive coil when the body RF coil is transmitting.

9. The MRI system of claim 1 wherein the detuning circuit, when in the enabled state, causes an impedance in its respective RF receive coil having a magnitude to prevent intercoil coupling between the plurality of RF receive coils in the array of RF receive coils.

10. The MRI system of claim 1 wherein the RF transmit coil and the array of RF receive coils form a parallel transmission coil arrangement when the detuning circuit is in the enabled state.

11. The MRI system of claim 1 wherein the array of RF receive coils comprises a plurality of overlaid coil loops.

12. A method for parallel transmission in an MRI system, the method comprising:
  causing a whole-body RF transmit coil to generate a first RF field during a transmit cycle of operation of the MRI system;
  causing an array of RF receive coils to generate a second time-varying RF field during the transmit cycle of operation of the MRI system, wherein causing the array of RF receive coils to generate the second time-varying RF field includes:
    enabling a detuning circuit coupled to the array of RF receive coils;
    selectively and dynamically controlling the detuning circuit to control an impedance and an off resonance in the detuning circuit, thereby also controlling an impedance and an off resonance in the array of RF receive coils while the whole-body RF transmit coil is transmitting;
    wherein the detuning circuit controls the impedance and the off resonance in the array of RF receive coils so as to cause the array of RF receive coils to generate the second time varying RF field during the transmit cycle of operation of the MRI system;
  upon completion of the transmit cycle, disabling the detuning circuit so as to cause the array of RF receive coils to receive RF resonance signals emitted from a subject generated in response to the first RF field and the second time-varying RF field; and
  storing the received RF resonance signals on a computer readable storage medium.

13. The method of claim 12 wherein enabling the detuning circuit comprises sending a DC control signal to an enabling diode in the detuning circuit.

14. The method of claim 12 wherein selectively controlling the detuning circuits comprises:
  sending a DC control signal to a varistor diode in the detuning circuit to control the off resonance of the detuning circuit; and
  sending at least one DC control signal to a variable attenuator in the detuning circuit to control the impedance of the detuning circuit.

15. The method of claim 14 wherein sending the at least one DC control signal to the variable attenuator dynamically controls the impedance of the detuning circuit.

16. The method of claim 12 wherein selectively controlling the detuning circuit comprises controlling the impedance of the detuning circuit such that a magnitude of the impedance in the array of RF receive coils is sufficient to prevent intercoil coupling in the array of RF receive coils.

17. An MRI system comprising:
  a main magnet having a bore there through;
  a plurality of gradient coils positioned about the bore of the main magnet;
  an RF transmit coil disposed within the bore of the main magnet and configured to generate a $B_1$ field during a transmit cycle of the MRI system, wherein the $B_1$ field excites nuclei of a subject positioned within the bore to generate RF resonance signals;
  an array of RF receive coils disposed within the bore of the main magnet and within a volume surrounded by the RF transmit coil; and
  a detuning circuit arrangement coupled to the array of RF receive coils to selectively cause the array of RF receive coils to operate in one of a transmit mode and a receive mode, the detuning circuit arrangement being configured to:
    operate in an enabled state during the transmit cycle of the MRI system so as to dynamically control impedance and off resonance in the array of RF receive coils, wherein operation of the detuning circuit arrangement in the enabled state causes the array of RF receive coils to generate a local $B_1$ field having a desired amplitude and phase; and
    operate in a disabled state during a receive cycle of the MRI system, wherein operation of the detuning circuit arrangement in the disabled state causes the array of RF receive coils to receive the RF resonance signals generated in response to the $B_1$ field and the local $B_1$ field.

18. The MRI system of claim 17 wherein the detuning circuit arrangement comprises a plurality of detuning circuits, and wherein each of the plurality of detuning circuits comprises a DC control system to dynamically control the impedance and the off resonance of a respective RF receive coil in the array of RF receive coils.

19. The MRI system of claim 18 wherein each of the plurality of detuning circuits comprises:
  an enabling diode configured to enable and disable the detuning circuit;
  a varactor diode to modify a capacitance in the detuning circuit, thereby controlling the off resonance of the detuning circuit; and
  a variable attenuator to control the impedance in the detuning circuit;
  wherein the DC control system is configured to generate DC signals to control each of the diode, the varactor diode, and the variable attenuator.

20. The MRI system of claim 18 wherein each of the plurality of detuning circuits, when in the enabled state, causes an impedance in a respective RF receive coil having a magnitude to prevent intercoil coupling in the array of RF receive coils.

21. The MRI system of claim 17 wherein the RF transmit coil and the array of RF receive coils form a parallel transmission coil arrangement when the detuning circuit is in the enabled state.

* * * * *